United States Patent
Mori et al.

(10) Patent No.: US 7,396,941 B2
(45) Date of Patent: Jul. 8, 2008

(54) METHOD FOR PRODUCING MONATIN

(75) Inventors: Ken-ichi Mori, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/505,997

(22) Filed: Aug. 18, 2006

(65) Prior Publication Data

US 2007/0066832 A1    Mar. 22, 2007

Related U.S. Application Data

(63) Continuation of application No. PCT/JP2005/000821, filed on Jan. 18, 2005.

(30) Foreign Application Priority Data

Feb. 27, 2004   (JP)   ............................. 2004-053717

(51) Int. Cl.
    *C07D 209/18*   (2006.01)
(52) U.S. Cl. ..................................... 548/495
(58) Field of Classification Search .................. 548/495
    See application file for complete search history.

(56) References Cited

U.S. PATENT DOCUMENTS

| 7,064,219 B2 | 6/2006 | Kawahara et al. |
| 2005/0020508 A1 | 1/2005 | Amino et al. |
| 2005/0137246 A1 | 6/2005 | Amino et al. |
| 2005/0272939 A1 | 12/2005 | Amino et al. |

FOREIGN PATENT DOCUMENTS

JP    2004-222657    8/2004
WO    03/059865    7/2003

OTHER PUBLICATIONS

Jerry March, Advanced Organic Chemistry, 4th edition, 1992, p. 896-7.*
Ebbers et al. Tetrahedron, 1997, vol. 53, 28, p. 9417-9476, (disclosed in IDS).*
Nakamura et al., Letters, 2000, vol. 2, 19, p. 2967-70, (disclosed in IDS).*
Nakamura, Kozo, et al., "Total Synthesis of Montain," Letters, vol. 2, No. 19, Jun. 23, 2000, pp. 2967-2970.
Holzapfel, C. W., "A Simple Cycloaddition Approach to A Racemate of the Natural Sweetner Monatin," Synthetic Communications, vol. 24, No. 22, 1994, pp. 3197-3211.
Ebbers, E. J., et al., "Controlled Racemization of Optically Active Organic Compounds: Prospects for Asymmetric Transformation," Tetrahedron, vol. 53, No. 28, 1997, pp. 9417-9476.
De Jesus Oliveria, D., et al., "Diastereoselective Formation Of A Quaternary Center In A Pyroglutamate Derivative. Formal Syntheis Of Monatin," Tetrahedron Letters, vol. 42, 2001, pp. 6793-6796.
U.S. Appl. No. 11/627,700, filed Jan. 26, 2007, Amino, et al.
U.S. Appl. No. 11/505,997, filed Aug. 18, 2006, Mori, et al.
Yamada, S., et al., "Method for the Racemization of Optically Active Amino Acids," J. Org. Chem., vol. 48, No. 6, 1983, pp. 843-846.

* cited by examiner

*Primary Examiner*—Kamal A Saeed
*Assistant Examiner*—Yong Chu
(74) *Attorney, Agent, or Firm*—Oblon, Spivak, McClelland, Maier & Neustadt, P.C.

(57) ABSTRACT

By simultaneously carrying out an isomerization reaction at position 2 of monatin in different configurations at positions 2 and 4 in the presence of an aldehyde under a condition of pH 4 to 11 in a mixture solvent of water and an organic solvent, and the crystallization of monatin in the same configurations at positions 2 and 4 or a salt thereof, monatin useful as a sweetener, particularly optically active monatin can efficiently be produced.

20 Claims, No Drawings

METHOD FOR PRODUCING MONATIN

CROSS-REFERENCE TO RELATED APPLICATIONS

The present application is a continuation of PCT/JP05/00821, filed on Jan. 18, 2005, and claims priority to JP 2004-053717, filed on Feb. 27, 2004.

TECHNICAL FIELD

The present invention relates to a method for producing monatin useful as a sweetener. More specifically, the invention relates to a method for efficiently producing optically active monatin.

BACKGROUND ART

4-Hydroxy-4-(3-indolylmethyl)-2-aminoglutaric acid (sometimes referred to as "monatin" hereinafter) in the form of (2S, 4S) as represented by the formula (5) is contained in the root skin of a plant Schlerochitom ilicifolius naturally occurring in a northern district of South Africa, namely Northern Transvaal. It is known that the compound in the form has a sweetness level several hundreds fold that of sucrose and is an amino acid derivative useful as a sweetener (see the official gazette of JP-A-64-25757).

(5)

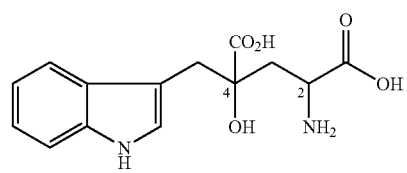

Monatin has two asymmetric carbon atoms at positions 2 and 4 and therefore includes the presence of four types of optical isomers.

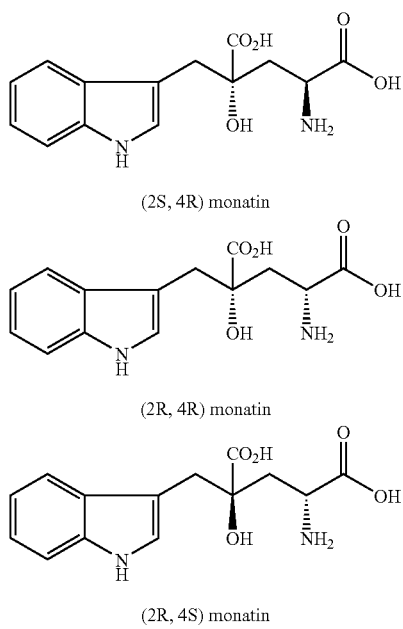

(2S, 4R) monatin (2R, 4R) monatin (2R, 4S) monatin

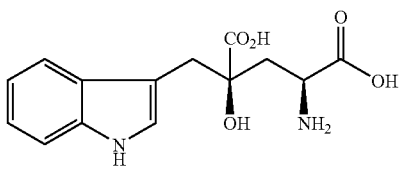

(2S, 4S) monatin

Various reports tell about methods for producing monatin (see for example Tetrahedron Letters, 2001, Vol. 42, No. 39, p 6793-6796; Organic Letters, 2000, Vol. 2, No. 19, p 2967-2970; Specification of U.S. Pat. No. 5,994,559; Synthetic Communication, 1994, Vol. 24, No. 22, p 3197-3211). Some examples tell about examinations of methods for producing optically active monatin. However, it cannot be said that these methods require such a great number of steps for the production that the methods are not methods industrially suitable.

Alternatively, the present applicant has recently found and has reported a method for producing a particular optically active monatin including a step of synthetically preparing a monatin precursor from indole-3-pyruvic acid to form a diastereomer salt with a particular optically active amine and a step of finally producing the particular optically active monatin via optical resolution (see the pamphlet of the International Application WO 03/059865). For example, (2R, 4R) monatin is listed. The method is represented by the following scheme.

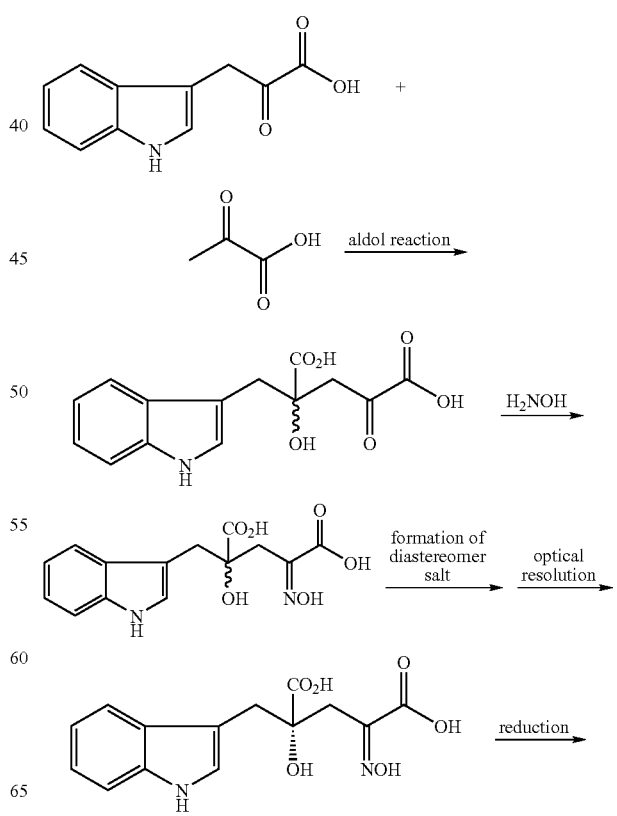

-continued

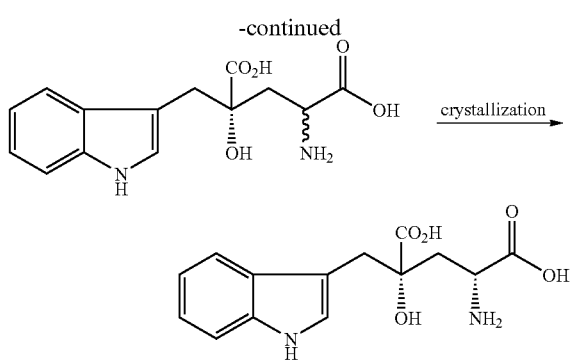

The production method requires a smaller number of steps compared with the traditional methods, by which an optically active monatin can be produced in an efficient manner and which is therefore a production method industrially suitable. However, the unintended optical isomer thereof at position 2 is eliminated into the mother liquid during the crystallization step. When the optical isomer can be isomerized and converted into the intended optically active monatin, the efficiency can be further raised.

As racemization methods of optically active amino acids, for example, methods by treatment under conditions with strong acids and strong alkalis or at higher temperature or racemization methods under relatively mild conditions in the presence of aldehydes have been known. According to these methods, the maximum yields are about 50%. Therefore, these methods cannot be said as efficient racemization methods. A method of racemization and deposition has been known for producing an intended optical isomer in combination with a particular optical isomer at a higher yield (see Tetrahedron, 1997, Vol. 53, No. 28, p 9417-9476). Enormous trials and errors are essential for finding out the combination.

DISCLOSURE OF THE INVENTION

It is an object of the invention to provide a method for efficiently producing monatin in the same configurations at positions 2 and 4 or a salt thereof.

As consequences of examinations and investigations, the present inventors found that by carrying out an isomerization reaction at position 2 of monatin in different configurations at positions 2 and 4 in the presence of an aldehyde under conditions of a specific solvent and a specific pH and simultaneous, selective deposition of an intended monatin in the same configurations at positions 2 and 4 alone, the equilibrium of the isomerization reaction is greatly inclined toward the intended optically active monatin so that the monatin can efficiently be produced. Thus, the invention has been achieved.

Specifically, the invention includes the following aspects.
[1] A method for producing monatin in the same configurations at positions 2 and 4 or a salt thereof, including a step of an isomerization reaction at position 2 of monatin in different configurations at positions 2 and 4 in a mixture solvent of water and an organic solvent in the presence of an aldehyde under a condition of pH 4 to 11 and simultaneous crystallization of monatin in the same configurations at positions 2 and 4 or a salt thereof.
[2] A method for producing monatin in the configuration (2R, 4R) or a salt thereof, including a step of an isomerization reaction at position 2 of monatin in the configuration (2S, 4R) in a mixture solvent of water and an organic solvent in the presence of an aldehyde under a condition of pH 4 to 11 and simultaneous crystallization of monatin in the configuration (2R, 4R) or a salt thereof.
[3] A method for producing monatin in the configuration (2S, 4S) or a salt thereof, including a step of an isomerization reaction at position 2 of monatin in the configuration (2R, 4S) in a mixture solvent of water and an organic solvent in the presence of an aldehyde under a condition of pH 4 to 11 and simultaneous crystallization of monatin in the configuration (2S, 4S) or a salt thereof.
[4] A method for producing (2R, 4R) monatin represented by the formula (2) or a salt thereof, including a step of an isomerization reaction at position 2 of (2S, 4R) monatin represented by the formula (1) in a mixture solvent of water and an organic solvent in the presence of an aldehyde under a condition of pH 4 to 11 and simultaneous crystallization of (2R, 4R) monatin or a salt thereof:

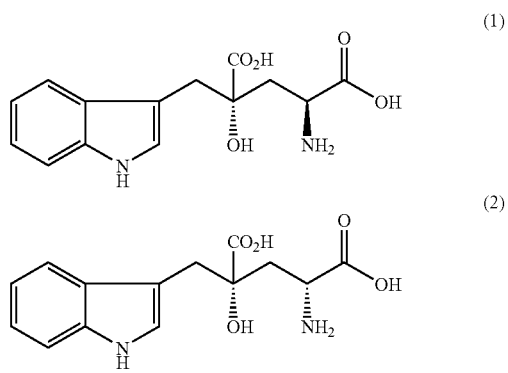

[5] A method for producing (2S, 4S) monatin represented by the formula (4) or a salt thereof, including a step of an isomerization reaction at position 2 of (2R, 4S) monatin represented by the formula (3) in a mixture solvent of water and an organic solvent in the presence of an aldehyde under a condition of pH 4 to 11 and simultaneous crystallization of (2S, 4S) monatin or a salt thereof:

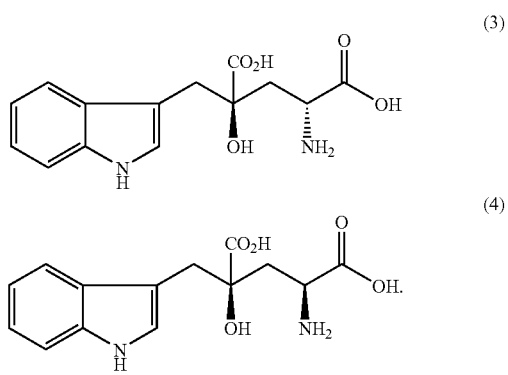

[6] A method for producing (2R, 4R) monatin represented by the formula (2) or a salt thereof, including a step of an isomerization reaction at position 2 of (2S, 4R) monatin represented by the formula (1) in a mixture of (2S, 4R) monatin and (2R, 4R) monatin in a mixture solvent of water and an organic solvent in the presence of an aldehyde under a condition of pH 4 to 11 and simultaneous crystallization of (2R, 4R) monatin or a salt thereof:

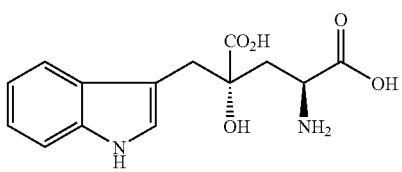

(1)

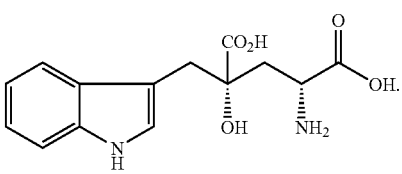

(2)

[7] A method for producing (2S, 4S) monatin represented by the formula (4) or a salt thereof, including a step of an isomerization reaction at position 2 of (2R, 4S) monatin represented by the formula (3) in a mixture of (2R, 4S) monatin and (2S, 4S) monatin in a mixture solvent of water and an organic solvent in the presence of an aldehyde under a condition of pH 4 to 11 and simultaneous crystallization of (2S, 4S) monatin or a salt thereof:

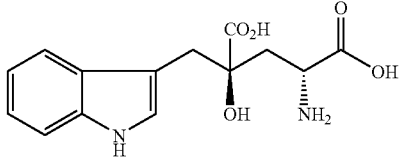

(3)

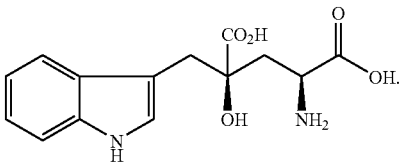

(4)

[8] A method described above in [1] through [7], where the organic solvent is alcohol.

[9] A method described above in [1] through [8], where the isomerization reaction and the crystallization are carried out under a condition of pH 4.5 to 10.

[10] A method described above in [1] through [8], where the isomerization reaction and the crystallization are carried out under a condition of pH 5 to 9.

In accordance with the invention, further, the phrase "same configurations at positions 2 and 4" means that the configurations at positions 2 and 4 are both R configurations or both S configurations, when the configurations are expressed by the R/S expression method. The phrase "different configurations at positions 2 and 4" means that either one of the configurations at positions 2 and 4 is S, while the remaining one thereof is R, when the configurations are expressed by the R/S expression method.

BEST MODE FOR CARRYING OUT THE INVENTION

The method for producing (2R, 4R) monatin or (2S, 4S) monatin in accordance with the invention includes a step of carrying out simultaneously the isomerization reaction at position 2 of (2S, 4R) monatin or (2R, 4S) monatin and the crystallization of (2R, 4R) monatin or (2S, 4S) monatin, in the presence of aldehyde, in a mixed solvent of water and organic solvent, and under the condition in which pH is from 4 to 11.

The monatin to be used for the method in accordance with the invention includes not only (2S, 4R) monatin or (2R, 4S) monatin singly existing but also mixtures of (2S, 4R) monatin and (2R, 4R) monatin at appropriate ratios and mixtures of (2R, 4S) monatin or (2S, 4S) monatin at appropriate ratios.

The method of the invention is particularly preferably used for intending the selective yield of (2R, 4R) monatin in monatin optically active at position 4 where (2S, 4R) monatin and (2R, 4R) monatin exist at an appropriate ratio or for intending the selective yield of (2S, 4S) monatin in monatin optically active at position 4 where (2R, 4S) monatin and (2S, 4S) monatin exist at an appropriate ratio.

The monatin to be used as a starting material for the method of the invention may be in any form of various salts, such as sodium salt, potassium salt and ammonium salt. Even the (2R, 4R) monatin and (2S, 4S) monatin obtained by the method of the invention may also be in any form of various salts.

The method for producing optically active monatin as described in the pamphlet of the International Publication WO 03/059865 is exemplified below. For example, (4S)-4-hydroxy-4-(3-indolylmethyl)-2-hydroxyiminoglutaric acid represented by the formula (6) is hydrogenated with a catalyst such as rhodium carbon, to obtain a reaction mixture containing (2R, 4S) monatin and (2S, 4S) monatin:

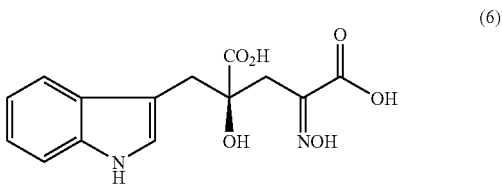

(6)

By filtering off the catalyst in the reaction mixture and then crystallizing the product in a mixture solvent of water and alcohol, (2S, 4S) monatin can be obtained selectively.

In this case, the (2R, 4S) monatin contained in the reaction mixture is eliminated into the mother liquid. However, the crystallization and isomerization reaction are simultaneously carried out under specific conditions according to the method of the invention to convert the (2R, 4S) monatin to the (2S, 4S) monatin, to obtain (2S, 4S) monatin in a more efficient manner.

The mother liquid remaining after the crystallization after the recovery of (2S, 4S) monatin from the reaction mixture of (2R, 4S) monatin and (2S, 4S) monatin contains (2R, 4S) monatin as an optical isomer at position 2 of the intended (2S, 4S) monatin, at a higher ratio than the intended monatin. The method of the invention is also applicable to the mother liquid, to isomerize (2R, 4S) monatin to (2S, 4S) monatin, which is then recovered from the mother liquid. Taking account of the efficiency of the isomerization reaction, the invention is preferably applied not to the reaction mixture before crystallization but to the mother liquid containing the intended isomer at a higher ratio after crystallization. As described above, the (2S, 4S) monatin crystal obtained from the mother liquid after crystallization by the method of the invention is recycled to any one of the steps of a series of the monatin processes, to raise the productivity. For example, the monatin crystal is added to the reaction mixture at the step of crystallizing the (2S, 4S) monatin from the reaction mixture of (2R, 4S) monatin and (2S, 4S) monatin, to more efficiently produce (2S, 4S) monatin. When the purity of the (2S, 4S) monatin crystal is high as obtained from the mother liquid after crystallization, the crystal may be mixed as it is with the crystal of (2S, 4S) monatin obtained by the crystallization from the reaction mixture.

The case of obtaining (2S, 4S) monatin is exemplified and described above. The same is true with the case of obtaining (2R, 4R) monatin.

According to the method of the invention, aldehyde is used for the isomerization reaction. As the aldehyde, aliphatic aldehyde or aromatic aldehyde may satisfactorily be used.

As the aliphatic aldehyde, there may be used saturated or unsaturated aldehydes with one to 7 carbon atoms, for example formaldehyde, acetoaldehyde, propionaldehyde, n-butylaldehyde, 1-butylaldehyde, n-valeraldehyde, capronaldhyde, n-heptylaldehyde, acrolein, and methacrolein.

As the aromatic aldehyde, there may be used for example benzaldehyde, salicylaldehyde, m-hydroxy-benzaldehyde, p-hydroxybenzaldehyde, o-nitrobenzaldehyde, p-nitrobenzaldehyde, 5-nitrosalicylaldehyde, anisealdehyde, o-vanillin, vanillin, furfural, and pyridoxal.

As the aldehyde, salicylaldehyde, pyridoxal and o-vanillin are particularly preferable.

Such aldehyde may be used within a range of 0.01 to 1 molar equivalent, preferably 0.05 to 0.5 molar equivalent to the monatin existing in the system.

The isomerization reaction and the crystallization according to the method of the invention are simultaneously carried out in the presence of aldehyde, while a mixture solvent of water and an organic solvent is used as the solvents (the reaction solvent and the crystallization solvents). As the organic solvent, an organic solvent miscible with water is used. Particularly, alcohols such as methanol, ethanol, propanol, and isopropanol are preferable. As the organic solvent, different two types of organic solvents may be mixed together and used. The ratio of an organic solvent and water is preferably set within a range of the ratio 1:0.01 to 1:1, more preferably 1:0.1 to 1:0.5 as the volume ratio of the organic solvent: water. When the ratio of water is higher, the crystallization likely involves more difficulty in the crystallization. When the ratio of the organic solvent is higher, disadvantageously, the raw material monatin tends to more hardly dissolve therein.

The temperature for the isomerization reaction and the crystallization is set within a range of preferably 0 to 100° C., more preferably 40 to 80° C. The duration of the isomerization reaction and the crystallization is set within a range of preferably 10 hours to 2 weeks, more preferably 15 hours to 10 days.

The pH is set within a range of 4 to 13, preferably 4.5 to 10, more preferably 5 to 9. The pH can be adjusted using an acid or an alkali. The acid includes for example but is not limited to organic acids such as acetic acid or inorganic acids such as hydrochloric acid and sulfuric acid. The alkali includes for example but is not limited to alkali metal hydroxides such as sodium hydroxide and potassium hydroxide or organic bases such as ammonia and amine. When the pH is too low, (2R, 4S) monatin or (2S, 4R) monatin is likely crystallized. When the pH is too high, disadvantageously, the crystal is likely to be hardly deposited.

The invention is now described in detail in the following Examples. However, the Examples never limit the invention. In the Examples, optical purity was measured by HPLC under the following conditions.

Column for Separating Optical Isomer
SUMICHIRAL OA-7100 manufactured by SUMIKA ANALYSIS CENTER Eluent
20 mM phosphate buffer (pH 2.8): acetonitrile=7:3

Column Temperature
10° C.

Flow Rate
0.6 ml/min

REFERENCE EXAMPLE 1

Production of 4-hydroxy-4-(3-indolylmethyl)-2-ketoglutaric acid

Indolepyruvic acid of 12.30 g (58.7 mmol at a purity of 97.0% by weight (abbreviated as wt % hereinafter)) was added to and dissolved in 2.45 g of sodium hydroxide dissolved in 209 mmol of water. 47.61 g of aqueous 25 wt % sodium hydroxide solution and a mixture solution of 25.85 g (293.5 mmol) of pyruvic acid and 25.85 g of water were added to the resulting solution in nitrogen atmosphere at 35° C. over 2 hours, while the reaction system was kept at pH 11.0. Then, the resulting mixture was agitated for 14 hours. In such manner, a reaction solution containing 4-hydroxy-4-(3-indolylmethyl)-2-ketoglutaric acid was obtained (the yield to indolepyruvic acid was 44.1%). 3.60 g of 1N hydrochloric acid was added to the reaction solution for neutralization (pH=6.91), to obtain a neutralized reaction solution of 275 ml.

168 ml of the neutralized reaction solution thus obtained was charged into a resin column (4.8-cm diameter) packed with 840 ml of a synthetic adsorbing agent (DIAION-SP207 manufactured by Mitsubishi Chemical), where pure water was eluted at a flow rate of 23.5 ml/min, to recover 1.7 to 2.9 L/L-R to obtain 4-hydroxy-4-(3-indolylmethyl)-2-ketoglutaric acid at a yield of 66.3%.

(NMR Spectrum) 1H-NMR(400 MHz, D2O)δ: 3.03 (d, 1H, J=14.6 Hz), 3.11(d, 1H, J=14.6 Hz), 3.21(d, 1H, J=18.1 Hz), 3.40(d, 1H, J=18.1 Hz), 7.06-7.15(m, 3H), 7.39(d, 1H, J=7.8 Hz), 7.66(d, 1H, J=7.8 Hz) 13C-NMR (400 MHz, D2O) δ: 35.43, 47.91, 77.28, 109.49, 112.05, 119.44, 119.67, 121.91, 125.42, 128.41, 136.21, 169.78, 181.43, 203.58 (Mass Analysis) ESI-MS theoretical value: C14H13NO6=291.07 ESI-MS experimental value: 290.02 [M-H]−

REFERENCE EXAMPLE 2

Production of 4-hydroxy-4-(3-indolylmethyl)-2-hydroxyiminoglutaric acid

Indole-3-pyruvic acid of 1.0 g (4.92 mmol) was added to and dissolved in 10 ml of aqueous saturated sodium carbonate solution. Then, the resulting solution was adjusted to pH 12.55, using aqueous 25% sodium hydroxide solution. After 1.3 g (14.8 mmol) of pyruvic acid was added to the solution, the resulting solution was adjusted to pH 12.6, using aqueous 25% sodium hydroxide solution, for reaction at ambient temperature for 2 hours, to obtain a reaction solution containing 4-hydroxy-4-(3-indolylmethyl)-2-ketoglutaric acid. While the solution was kept around neutral pH, using aqueous 25% sodium hydroxide solution, 1.37 g (19.7 mmol) of hydroxylamine hydrochloride salt was added to the solution, for agitation at ambient temperature for 4 hours. Using conc. hydrochloric acid, the reaction solution was adjusted to acidic pH, for extraction of organic matters into ethyl acetate. The organic layer was rinsed with saturated aqueous sodium chloride and dried over anhydrous magnesium sulfate. Then, the resulting layer was concentrated, to obtain the residue. The residue was recrystallized in aqueous 28% ammonia and ethanol, to obtain the crystalline ammonium salt (0.52 g; 1.5 mmol) of 4-hydroxy-4-(3-indolylmethyl)-2-hydroxyiminoglutaric acid (at a yield of 31% vs. indole-3-pyruvic acid).

(NMR Spectrum) 1HNMR (DMSO-d6)δ: 2.66(s, 2H), 2.89(d, J=14.4 Hz, 1H), 3.04(d, J=14.4 Hz, 1H), 6.89-6.94(m, 1H), 6.97-7.03(m, 1H), 7.11(d, J=2.8 Hz, 1H), 7.27(d, J=7.8 Hz, 1H), 7.53(d, J=7.8 Hz, 1H), 10.71(br s, 1H) (Mass Analysis) ESI-MS theoretical value: C14H14N2O6=306.28 ESI-MS experimental value: 305.17 [M-H]–

REFERENCE EXAMPLE 3

Production of 4-hydroxy-4-(3-indolylmethyl)-2-hydroxyiminoglutaric acid

Indole-3-pyruvic acid of 10.0 g (49.2 mmol) was added to and dissolved in 98 ml of aqueous saturated sodium carbonate solution. Then, the resulting solution was adjusted to pH 12.4, using aqueous 25% sodium hydroxide solution. After 16.3 g (147.6 mmol) of sodium pyruvate was added to the solution, the resulting mixture reacted together at ambient temperature for 2 hours, to obtain a reaction solution containing 4-hydroxy-4-(3-indolylmethyl)-2-ketoglutaric acid. While the solution was kept around neutral pH, using aqueous 25% sodium hydroxide solution, 13.7 g (197 mmol) of hydroxylamine hydrochloride salt was added to the solution, for agitation at ambient temperature for 4 hours. Using conc. hydrochloric acid, the reaction solution was adjusted to acidic pH, for extraction of organic matters into ethyl acetate. The organic layer was rinsed with saturated aqueous sodium chloride and dried over anhydrous magnesium sulfate. Then, the resulting layer was concentrated, to obtain the residue. The residue was recrystallized in aqueous 28% ammonia and ethanol, to obtain the crystalline di-ammonium salt (5.51 g; 16.2 mmol) of 4-hydroxy-4-(3-indolylmethyl)-2-hydroxyiminoglutaric acid (at a yield of 32% vs. indole-3-pyruvic acid).

REFERENCE EXAMPLE 4

Production of 4-hydroxy-4-(3-indolylmethyl)-2-hydroxyiminoglutaric acid

Indole-3-pyruvic acid of 73.8 g (352 mmol) was added to and dissolved in 917 ml of aqueous 1.6 wt % sodium hydroxide solution. Then, the resulting reaction solution was adjusted to 35° C. While the solution was kept at pH 11.1, using aqueous 30% sodium hydroxide solution, 310.2 g (1761 mmol) of aqueous 50% pyruvic acid solution was dropwise added to the mixture over 2 hours. After reaction for another 4.5 hours, a reaction solution containing 4-hydroxy-4-(3-indolylmethyl)-2-ketoglutaric acid was obtained. While the solution was kept at pH 7, using aqueous 30% sodium hydroxide solution, 367.2 g (2114 mmol) of 40% hydroxylamine hydrochloride salt solution was added to the solution, for agitation at 5° C. for 17.5 hours. Using conc. hydrochloric acid, the reaction solution was adjusted to pH 2, for extraction of organic matters into ethyl acetate. The organic layer was rinsed with saturated aqueous sodium chloride and concentrated, to obtain the residue. The residue was recrystallized in 60 ml of aqueous 28% ammonia and 1350 ml of 2-propanol, to obtain the crystalline di-ammonium salt (43.4 g; 142 mmol) of 4-hydroxy-4-(3-indolylmethyl)-2-hydroxyiminoglutaric acid a yield of 40% vs. indole-3-pyruvic acid).

REFERENCE EXAMPLE 5

Production of (R)-(+)-1-phenylethylamine salt of (4S)-4-hydroxy-4-(3-indolylmethyl)-2-hydroxyiminoglutaric 44.7 g (0.131 mol) of the ammonium salt of 4-hydroxy-4-(3-indolylmethyl)-2-hydroxyiminoglutaric acid was dissolved in 500 ml of water at 25° C. The resulting aqueous solution was adjusted to pH 2, using 25.5 g of 36% hydrochloric acid. The acidic solution was extracted in 1300 ml of ethyl acetate. The ethyl acetate solution was rinsed with 200 ml of aqueous saturated sodium chloride. 500 ml of aqueous sodium carbonate solution (13.9 g (0.131 mol) of sodium carbonate) was added to the resulting ethyl acetate solution, for agitation to separate the aqueous alkaline solution from ethyl acetate. 23.1 g of 36% hydrochloric acid was added to the resulting aqueous alkaline solution to adjust the solution to pH 2. (R)-(+)-1-phenylethylamine of 6.99 g (57.6 mmol) is dropwise added to the resulting acidic solution, for agitation at 25° C. for one hour. The resulting crystal was filtered and dried under reduced pressure, to obtain the (R)-(+)-1-phenylethylaine salt (21.8 g; 47.8 mmol) of (4S)-4-hydroxy-4-(3-indolylmethyl)-2-hydroxyiminoglutaric acid (at a yield of 72.7% and optical purity of 87.4%).

1H-NMR(400 MHz, DMSO-d6)δ: 1.48 (d, 3H, J=6.8 Hz), 2.63(d, 1H, J=14.0 Hz), 2.70(d, 1H, J=14.0 Hz), 2.90(d, 1H, J=14.1 Hz), 3.06(d, 1H, J=14.1 Hz), 4.40(q, 1H, J=6.8 Hz), 6.91-7.54(m, 10H)

REFERENCE EXAMPLE 6

Production of (s)-(–)-1-phenylethylamine salt of (4R)-4-hydroxy-4-(3-indolylmethyl)-2-hydroxyiminoglutaric 7.12 g (58.7 mol) of (S)-(–)-1-phenylethylamine was further dropwise added to the filtrate after the crystal was separated, as obtained in Example 5, for agitation at 25° C. for one hour. The resulting crystal was filtered and dried under reduced pressure, to obtain dried under reduced pressure, to obtain the (S)-(–)-1-phenylethylamine salt (23.8 g; 53.3 mmol) of (4R)-4-hydroxy-4-(3-indolylmethyl)-2-hydroxyiminoglutaric acid (at a yield of 81.1% and optical purity of 92.1%)

REFERENCE EXAMPLE 7a

Production of ammonium salt of (4S)-4-hydroxy-4-(3-indolylmethyl)-2-hydroxyiminoglutaric acid Water of 200 ml and 18.5 g of aqueous 28% ammonia were added to 21.8 g (51.0 mol) of (R)-(+)-1-phenylethylamine salt of (4S)-4-hydroxy-4-(3-indolylmethyl)-2-hydroxyiminoglutaric acid, to dissolve the acid, to which 200 ml of toluene was added for agitation. The aqueous layer after extraction was heated to 60° C. To the resulting aqueous solution was dropwise added 900 ml of 2-propanol over 2 hours. The resulting aqueous 2-propanol solution was cooled to 10° C. over 5 hours. Then, agitation was done at 10° C. for 10 hours. The resulting crystal was filtered and dried under reduced pressure, to obtain 14.75 g of the ammonium salt of (4S)-4- hydroxy-4-(3-indolylmethyl)-2-hydroxyiminoglutaric acid (at a yield of 85.1% and optical purity of 99.0%).

Melting point: 205° C. (decomposed) Specific rotation: [α]20D+13.4 (c=1.00, H2O)

REFERENCE EXAMPLE 7b

Production of ammonium salt of (4R)-4-hydroxy-4-(3-indolylmethyl)-2-hydroxyiminoglutaric acid As described above in the Reference Example, 16.2 g of the ammonium salt of (4R)-4-hydroxy-4-(3-indolylmethyl)-2-hydroxyiminoglutaric acid was obtained from 23.8 g (53.3 mmol) of the (R)-(+)-1-phenylethylamine salt of (4R)-4-hydroxy-4-(3-indolylmethyl)-2-hydroxyiminoglutaric acid a yield of 89.3% and optical purity of 99.9%).

Specific rotation: [α]20D -13.6 (c=1.00, H2O)

REFERENCE EXAMPLE 8

Production of (2R, 4R) monatin 13.2 g (38.7 mmol) of the ammonium salt of (4R)-4-hydroxy-4-(3-indolylmethyl)-2-hydroxyiminoglutaric aci obtained in Reference Example 7b was added to and dissolved in 135 ml of aqueous 28% ammonia, to which 6.93 g of 5% rhodium carbon (50%-wet product) was added for reaction at a hydrogen pressure of 1 MPa and 25° C. 24 hours later, the catalyst was filtered off (through a 0.2-micron filter). 2.54 g (18.4 mmol) of potassium carbonate was dissolved in the resulting filtrate. The solution was concentrated. Water of 20 ml and 45 ml of ethanol were added to 32.7 g of the resulting concentrate, for agitation at 25° C., to which 60 ml of ethanol was dropwise added over 3 hours. Then, agitation was done at 25° C. for 20 hours for crystallization. The resulting wet crystal of 9.78 g was dissolved in 12 ml of water, to which 24 ml of ethanol was added and 51 ml of ethanol was additionally dropwise added over 3 hours. The ethanol solution was cooled to 15° C. over 4 hours, for agitation at 15° C. for 10 hours. The resulting wet crystal at 7.08 g was dried under reduced pressure, to obtain 5.7 g of the potassium salt of the intended (2R, 4R) monatin.

1HNMR (400 MHz, D2O) δ: 2.06(dd, J=11.8, 15.3 Hz, 1H), 2.67(dd, J=2.0, 15.2 Hz, 1H), 3.08(d, J=14.4 Hz, 1H), 3.28(d, J=14.4 Hz, 1H), 3.63(dd, J=2.2, 12.2 Hz, 1H), 7.12-7.16(m, 1H), 7.20-7.24(m, 2H), 7.48-7.49(m, 1H), 7.71-7.73 (m, 1H) ESI-MS theoretical value: C14H16N2O5=292.29 ESI-MS experimental value: 291.28 [M-H]−

EXAMPLE 1

The mother liquid of 170 g for crystallization, as obtained in Reference Example 8, was concentrated to 25 g (containing 6.65 g (19.1 mmol) of monatin; (2S, 4R): (2R, 4R)=74:26), which was then adjusted to pH 6.6, using 0.69 g of 35% hydrochloric acid. 0.467 g (3.82 mmol) of salicylaldehyde was added to the resulting solution, to which 25 ml of ethanol was added for agitation in nitrogen purge at 65° C. for 189 hours, for simultaneous isomerization reaction and crystallization. During the reaction, the reaction solution was periodically adjusted to pH 6.6, using 35% hydrochloric acid. The composition ratio of monatin in the reaction solution in slurry was (2S, 4R): (2R, 4R)=11:89. The resulting crystal was separated via filtration (wet crystal of 5.14 g), and dried under reduced pressure, to obtain the potassium salt (3.98 g; 11.0 mmol) of the intended (2R, 4R) monatin (purity of 99.3% by HPLC).

EXAMPLE 2

Using 0.788 g (3.82 mmol) of pyridoxal hydrochloride salt instead of salicylaldehyde used in Example 1, agitation was done at 65° C. for 18 hours, for simultaneous isomerization reaction and crystallization. The composition ratio of monatin in the reaction solution in slurry was (2S, 4R): (2R, 4R)=34:66. The resulting crystal was separated via filtration, to obtain a wet crystal of 19 g. The composition ratio of monatin in the wet crystal was (2S, 4R): (2R, 4R)=27:73.

REFERENCE EXAMPLE 9

Production of mixture of (2R, 4R) monatin and (2S, 4S) monatin

The ammonium salt (7.0 g; 20.6 mmol) of 4-hydroxy-4-(3-indolylmethyl)-2-hydroxyiminoglutaric acid as obtained in Reference Example 4 was dissolved in 60 ml of aqueous 28% ammonia, to which 3.69 g of 5% rhodium carbon (50%-wet product) was added for reaction at a hydrogen pressure of 1 MPa and 25° C. 24 hours later, the catalyst was filtered off (through a 0.2-micron filter). The resulting solution was concentrated. Water of 28.8 ml and 1.18 g of acetic acid were added to 28.2 g of the resulting concentrate, for agitation at 25° C. for 1.5 hours, for crystallization. The resulting crystal was filtered and separated, to obtain a wet crystal of 7.77 g. The wet crystal was dried under reduced pressure, to obtain the free form (5.45 g) of an intended mixture of (2R, 4R) monatin and (2S, 4S) monatin (purity of 87.3%).

1HNMR (400 MHz, D2O) δ: 2.06(dd, J=11.8, 15.3 Hz, 1H), 2.67(dd, J=2.0, 15.2 Hz, 1H), 3.08(d, J=14.4 Hz, 1H), 3.28(d, J=14.4 Hz, 1H), 3.63(dd, J=2.2, 12.2 Hz, 1H), 7.12-7.16(m, 1H), 7.20-7.24(m, 2H), 7.48-7.49(m, 1H), 7.71-7.73 (m, 1H) ESI-MS theoretical value: C14H16N2O5=292.29 ESI-MS experimental value: 291.28 [M-H]−

EXAMPLE 3

The mother liquid of 55.2 g for crystallization as obtained in Reference Example 9 was concentrated to 7.7 g (containing 2.00 g (5.77 mmol) of monatin; (2S, 4R): (2R, 4S): (2R, 4R): (2S, 4S) =84.6:84.6:15.4:15.4), which was then adjusted to pH 5, using 1.17 g of acetic acid. Salicylaldehyde of 0.141 g (1.15 mmol) was added and then, 17.5 ml of methanol was added for agitation in nitrogen stream at 65° C. for 143 hours, for simultaneous isomerization reaction and crystallization. During the reaction, the reaction solution was periodically adjusted to pH 5, using acetic acid. The composition ratio of monatin in the reaction solution in slurry was (2S, 4R): (2R, 4S): (2R, 4R): (2S, 4S)=18.6:18.6:81.4:81.4. The resulting crystal was separated via filtration (wet crystal of 1.95 g), and dried under reduced pressure, to obtain the crystal (1.31 g) of the free form of a monatin mixture (at a yield of 69.8%). The composition ratio of monatin was (2S, 4R): (2R, 4S): (2R, 4R): (2S, 4S)=13.0:13.0:87.0:87.0.

Then, 1.31 g of the crystal obtained above was combined with 5.45 g of the crystal obtained in Reference Example 9. The mixture was then dispersed in 15 ml of water, to which 2.42 ml of aqueous 8N sodium hydroxide solution was added for dissolution. 15 ml of methanol was added to the resulting solution at 35° C., to which 70 ml of methanol was further dropwise added over 2 hours. After the completion of the dropwise addition, the methanol solution was cooled to 10° C. over 2.5 hours, for agitation at 10° C. for 30 minutes for crystallization. The resulting crystal was filtered and separated (wet crystal at 5.47 g), dried under reduced pressure, to obtain the sodium salt (4.24 g) of an intended mixture of (2R, 4R) monatin and (2S, 4S) monatin (at purity of 99.1%)

1HNMR (400 MHz, D2O) δ: 2.06(dd, J=11.8, 15.3 Hz, 1H), 2.67(dd, J=2.0, 15.2 Hz, 1H), 3.08(d, J=14.4 Hz, 1H), 3.28(d, J=14.4 Hz, 1H), 3.63(dd, J=2.2, 12.2 Hz, 1H), 7.12-7.16 (m, 1H), 7.20-7.24(m, 2H), 7.48-7.49(m, 1H), 7.71-7.73 (m, 1H) ESI-MS theoretical value: C14H16N2O5=292.29 ESI-MS experimental value: 291.28 [M-H]−

COMPARATIVE EXAMPLE 1

The mother liquid of 170 g for crystallization as obtained in Reference Example 8 was concentrated to 25 g (containing 6.65 g (19.1 mmol) of monatin; (2S, 4R): (2R, 4R)=74:26), which was then adjusted to pH 14, using 1.75 g of 50% potassium hydroxide. 0.467 g (3.82 mmol) of salicylaldehyde was added to the resulting solution, to which 25 ml of ethanol was added for agitation at 65° C. for 64 hours. However, no crystal was deposited. The composition ratio of monatin in the reaction solution was (2S, 4R): (2R, 4R)=45:55.

INDUSTRIAL APPLICABILITY

In accordance with the invention, monatin with different configurations at positions 2 and 4 can be derivatized into an intended monatin with the same configurations at positions 2 and 4 via isomerization reaction in an efficient manner. Thus, (2R, 4R) monatin and (2S, 4S) monatin can efficiently be produced, industrially advantageously.

The present application is based on Japanese Patent Application 2004-053717 filed in Japan, the contents of which are all encompassed within the specification.

The invention claimed is:

1. A method for producing monatin which has the same configurations at positions 2 and 4 or a salt thereof,
said method comprising:
isomerizing position 2 of monatin which has different configurations at positions 2 and 4 in a mixed solvent of water and an organic solvent comprising an alcohol in the presence of an aldehyde under a condition of pH 4 to 11 and simultaneously crystallizing said monatin which has the same configurations at positions 2 and 4 or salt thereof.

2. A method according to claim 1, wherein said monatin which has the same configurations at positions 2 and 4 or salt thereof is monatin which has the configuration (2R, 4R) or a salt thereof, and
wherein said monatin which has different configurations at positions 2 and 4 is monatin which has the configuration (2S, 4R).

3. A method according to claim 1, wherein said monatin which has the same configurations at positions 2 and 4 or salt thereof is monatin which has the configuration (2S, 4S) or a salt thereof, and
wherein said monatin which has different configurations at positions 2 and 4 is monatin which has the configuration (2R, 4S).

4. A method according to claim 1, wherein said monatin which has the same configurations at positions 2 and 4 or salt thereof is (2R, 4R) monatin represented by formula (2) or a salt thereof:

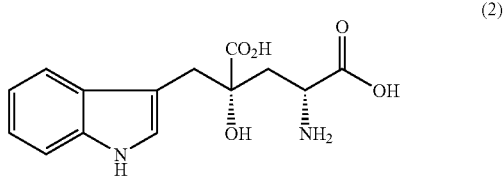

and
herein said monatin which has different configurations at positions 2 and 4 is (2S, 4R) monatin represented by formula (1):

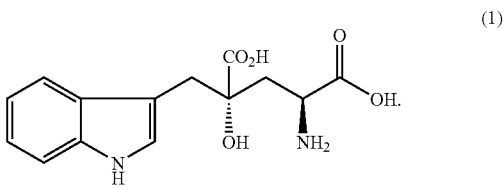

5. A method according to claim 1, wherein said monatin which has the same configurations at positions 2 and 4 or salt thereof is (2S, 4S) monatin represented by formula (4) or a salt thereof:

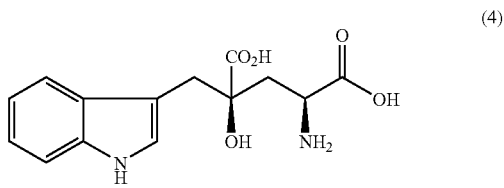

and
wherein said monatin which has different configurations at positions 2 and 4 is (2R, 4S) monatin represented by formula (3):

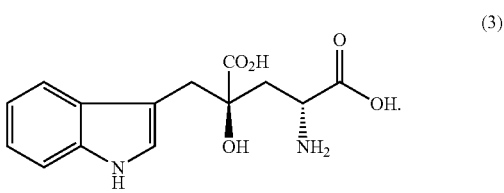

6. A method for producing (2R, 4R) monatin represented by formula (2) or a salt thereof:

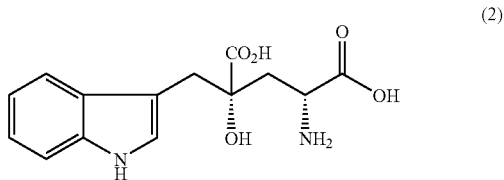

said method comprising:

isomerizing position 2 of (2S, 4R) monatin represented by formula (1):

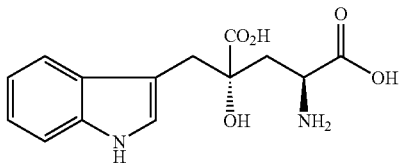
(1)

in a mixture of (2S, 4R) monatin and (2R, 4R) monatin in a mixed solvent of water and an organic solvent comprising an alcohol in the presence of an aldehyde under a condition of pH 4 to 11 and simultaneously crystallizing said (2R, 4R) monatin of formula (2) or salt thereof.

7. A method for producing (2S, 4S) monatin represented by formula (4) or a salt thereof:

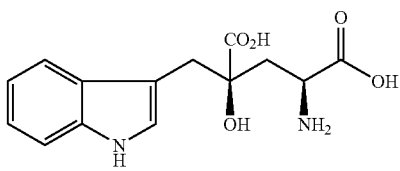
(4)

said method comprising:
isomerizing position 2 of (2R, 4S) monatin represented by formula (3):

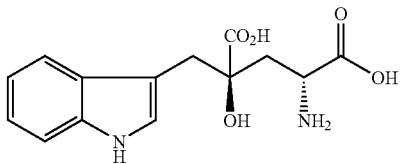
(3)

in a mixture of (2R, 4S) monatin and (2S, 4S) monatin in a mixed solvent of water and an organic solvent comprising an alcohol in the presence of an aldehyde under a condition of pH 4 to 11 and simultaneously crystallizing said (2S, 4S) monatin of formula (4) or salt thereof.

8. A method according to claim 1, wherein said organic solvent is an alcohol.

9. A method according to claim 2, wherein said organic solvent is an alcohol.

10. A method according to claim 3, wherein said organic solvent is an alcohol.

11. A method according to claim 4, wherein said organic solvent is an alcohol.

12. A method according to claim 5, wherein said organic solvent is an alcohol.

13. A method according to claim 6, wherein said organic solvent is an alcohol.

14. A method according to claim 7, wherein said organic solvent is an alcohol.

15. A method according to claim 1, wherein said isomerizing and said crystallizing are carried out at a pH of 4.5 to 10.

16. A method according to claim 6, wherein said isomerizing and said crystallizing are carried out at a pH of 4.5 to 10.

17. A method according to claim 1, wherein said isomerizing and said crystallizing are carried out at a pH of 5 to 9.

18. A method according to claim 6, wherein said isomerizing and said crystallizing are carried out at a pH of 5 to 9.

19. A method according to claim 7, wherein said isomerizing and said crystallizing are carried out at a pH of 4.5 to 10.

20. A method according to claim 7, wherein said isomerizing and said crystallizing are carried out at a pH of 5 to 9.

* * * * *

UNITED STATES PATENT AND TRADEMARK OFFICE
CERTIFICATE OF CORRECTION

PATENT NO. : 7,396,941 B2  
APPLICATION NO. : 11/505997  
DATED : July 8, 2008  
INVENTOR(S) : Ken-ichi Mori et al.

Page 1 of 1

It is certified that error appears in the above-identified patent and that said Letters Patent is hereby corrected as shown below:

Column 10, line 4, "acid a yield"  should read -- acid at a yield --;  
line 9, "noglutaric"  should read -- noglutaric acid --.

Column 11, line 24, "-hydroxyiminoglutaric aci"  
should read -- -hydroxyiminoglutaric acid --.

Signed and Sealed this

Twenty-fourth Day of February, 2009

JOHN DOLL  
*Acting Director of the United States Patent and Trademark Office*